United States Patent
Zhu et al.

(10) Patent No.: US 11,830,111 B2
(45) Date of Patent: Nov. 28, 2023

(54) MAGNETIC RESONANCE IMAGING METHOD, DEVICE, MEDICAL DEVICE AND STORAGE MEDIUM

(71) Applicant: Shenzhen Institutes of Advanced Technology, Guangdong (CN)

(72) Inventors: Yanjie Zhu, Guangdong (CN); Yuanyuan Liu, Guangdong (CN); Dong Liang, Guangdong (CN); Xin Liu, Guangdong (CN); Hairong Zheng, Guangdong (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 753 days.

(21) Appl. No.: 17/047,062

(22) PCT Filed: May 17, 2018

(86) PCT No.: PCT/CN2018/087194
§ 371 (c)(1),
(2) Date: Oct. 12, 2020

(87) PCT Pub. No.: WO2019/153566
PCT Pub. Date: Aug. 15, 2019

(65) Prior Publication Data
US 2021/0166442 A1 Jun. 3, 2021

(30) Foreign Application Priority Data
Feb. 12, 2018 (CN) .......................... 201810145141.0

(51) Int. Cl.
*G06T 11/00* (2006.01)
*G01R 33/56* (2006.01)
(Continued)

(52) U.S. Cl.
CPC .......... *G06T 11/005* (2013.01); *G01R 33/561* (2013.01); *G01R 33/5608* (2013.01); *G06T 11/006* (2013.01); *A61B 5/055* (2013.01)

(58) Field of Classification Search
CPC . G06T 11/005; G06T 11/006; G01R 33/5608; G01R 33/561; A61B 5/055
See application file for complete search history.

(56) References Cited

FOREIGN PATENT DOCUMENTS

| CN | 103472419 A | * 12/2013 |
|----|-------------|-----------|
| CN | 103472419 A | 12/2013 |

(Continued)

OTHER PUBLICATIONS

International Search Report of PCT/CN2018/087194.
Written Opinion of PCT/CN2018/087194.

*Primary Examiner* — Wednel Cadeau

(57) ABSTRACT

Provided are a method and device for magnetic resonance parameter imaging, medical equipment, and a storage medium. The method comprises: performing acceleration sampling with respect to an image to be reconstructed of an observation target in a preset parameter direction to acquire K-space data corresponding to the image to be reconstructed, calculating, on the basis of the K-space data and of a parameter relaxation model, a parameter value and a compensation coefficient of the image to be reconstructed, generating, on the basis of the compensation coefficient, a compensation image corresponding to the image to be reconstructed, calculating, on the basis of the compensation image, respectively a low-rank part and a sparse part of the image to be reconstructed so as to update the compensation image.

10 Claims, 3 Drawing Sheets

(51) Int. Cl.
*G01R 33/561* (2006.01)
*A61B 5/055* (2006.01)

(56) References Cited

FOREIGN PATENT DOCUMENTS

| | | |
|---|---|---|
| CN | 104360295 A | 2/2015 |
| CN | 106232003 A | 12/2016 |
| CN | 106618571 A | 5/2017 |
| WO | 0141639 A1 | 6/2001 |

* cited by examiner

MAGNETIC RESONANCE IMAGING METHOD, DEVICE, MEDICAL DEVICE AND STORAGE MEDIUM

TECHNICAL FIELD

The invention belongs to the field of magnetic resonance imaging technology, and particularly involves a magnetic resonance imaging method, device, medical device and storage medium.

BACKGROUND

Quantitative magnetic resonance imaging differentiates different tissues by quantitative analysis of some intrinsic parameters of different tissues in the human body, such as, longitudinal relaxation time $T_1$, transverse relaxation time $T_2$, proton density, and longitudinal relaxation time in the rotating frame $T_{1\rho}$, to provide more accurate diagnostic information for doctors, so it has been widely applied to clinical practice. However, during the magnetic resonance imaging, images of multiple different parameter direction values (i.e. TE (echo time) and TSL (spin-lock time)) needs to be acquired, so it requires long scan time, which has become a bottleneck restricting the clinical development of quantitative magnetic resonance imaging.

In order to reduce the scan time, the current commercial fast imaging techniques mainly include partial Fourier (PF) and parallel imaging (i.e. sensitivity encoding (SENSE) and Generalized Autocalibrating Partially Parallel Acquisition (GRAPPA)). In recent years, compressed sensing technology based on sparse sampling theory has been widely concerned and applied. These techniques aim to obtain a similar parameter map or a parameter map without obvious artifacts by developing redundancy in image or K-space data. Therefore, the quality of the obtained parameter map is highly dependent on the parametric imaging method adopted. Traditional rapid parametric imaging methods usually comprise two phases: reconstruction and fitting. In the reconstruction phase, a parameter-weighted image is reconstructed from undersampled data. In the fitting phase, the parameter image is obtained by fitting from the reconstructed the parameter-weighted image through the established relaxation model. However, there are some errors between the reconstructed parameter-weighted image and the actual image. These errors are transmitted to the subsequent fitting phase and further affect the fitted image.

SUMMARY OF THE INVENTION

The invention provides a magnetic resonance imaging method, device, medical device and storage medium, aiming at solving the problems of long scan time and low imaging precision of the magnetic resonance imaging method with the existing technology.

On the one hand, the invention provides a magnetic resonance imaging method, which comprises the following steps:

conducting accelerated sampling on the image of the preset observed target to be reconstructed under the preset parameter direction to obtain the corresponding K-space data of the said image to be reconstructed;

calculating the initial parameter value and compensation coefficient of the said image to be reconstructed according to the said K-space centerdata and the preset parametric relaxation model;

generating the corresponding compensated image of the said image to be reconstructed according to the said compensation coefficient and calculate the low-rank component and the sparse component of the said image to be reconstructed according to the said compensated image;

updating the compensated image according to the said low-rank component and the said sparse component, and judge whether the update of the said compensated image converges. If the update converges, updating the said image to be reconstructed according to the said updated compensated image; otherwise, skipping to the step of calculating the low-rank component and the sparse component of the said image to be reconstructed respectively;

judging whether the update of the said image to be reconstructed converges. If the update converges, fitting and outputting the parameter map of the said observed target according to the said parametric relaxation model and the updated image to be reconstructed, otherwise, calculating the parameter value and compensation coefficient of the updated image to be reconstructed according to the said parametric relaxation model, and skipping to the step of generating the corresponding compensated image of the said image to be reconstructed according to the said compensation coefficient.

On the other hand, the invention provides a magnetic resonance imaging device, which comprises:

Accelerated sampling unit is used to conduct accelerated sampling on the image of the preset observed target to be reconstructed under the preset parameter direction to obtain the corresponding K-space data of the said image to be reconstructed;

Coefficient calculation unit is used to calculate the parameter value and compensation coefficient of the said image to be reconstructed according to the said K-space data and the preset parametric relaxation model;

Image compensation unit is used to generate the corresponding compensated image of the said image to be reconstructed according to the said compensation coefficient and calculate the low-rank component and the sparse component of the said image to be reconstructed according to the compensated image;

Image update unit is used to update the compensated image according to the said low-rank component and the said sparse component, and judge whether the update of the said compensated image converges. If the update converges, the said image to be reconstructed is updated according to the said updated compensated image; otherwise, the image compensation unit is triggered to execute the step of calculating the low-rank component and the sparse component of the said image to be reconstructed respectively; and Fitting and outputting unit is used to judge whether the update of the said image to be reconstructed converges. If the update converges, the parameter map of the said observed target is fitted and output according to the said parametric relaxation model and the said updated image to be reconstructed, otherwise the parameter value and compensation coefficient of the updated image to be reconstructed is calculated according to the said parametric relaxation model, and the said image compensation unit is triggered to execute the step of generating the corresponding compensated image of the said image to be reconstructed according to the said compensation coefficient.

In addition, the invention also provides a medical device, which comprises a memory, a processor, and a computer program stored in the memory and capable of running on the said processor, which executes the said computer program to implement said steps of the aforesaid magnetic resonance imaging method.

Moreover, the invention also provides a computer readable storage medium, which stores a computer program, which is executed by the processor to implement the said steps of the aforesaid magnetic resonance imaging method.

The method comprises the following steps: conducting accelerated sampling on the image of the observed target to be reconstructed under the preset parameter direction to obtain the corresponding K-space data of the image to be reconstructed, calculating the parameter value and compensation coefficient of the image to be reconstructed according to the K-space data and the parametric relaxation model, generating the corresponding compensated image of the image to be reconstructed according to the compensation coefficient, calculating the low-rank component and the sparse component of the image to be reconstructed according to the compensated image to update the compensated image for several times, updating the image to be reconstructed according to the updated compensated image, fitting and outputting the parameter map of the observed target when the update of the image to be reconstructed converges, or calculating the parameter value and compensation coefficient of the updated image to be reconstructed according to the parametric relaxation model, and skipping to the steps to generate the corresponding compensated image of the image to be reconstructed according to the compensation coefficient, thus to effectively improve the efficiency and accuracy of magnetic resonance imaging.

DETAILED DESCRIPTIONS

In order to make the objectives, technical solutions, and advantages of the present invention clearer, the present invention is further described in detail below with reference to the accompanying figures and embodiments. It should be appreciated that the specific embodiments described herein are merely illustrative of the present invention; it is not intended to limit the present invention.

The detailed description of the implementation of the invention made in accordance with embodiments is as follows:

Embodiment 1

Figure 1:
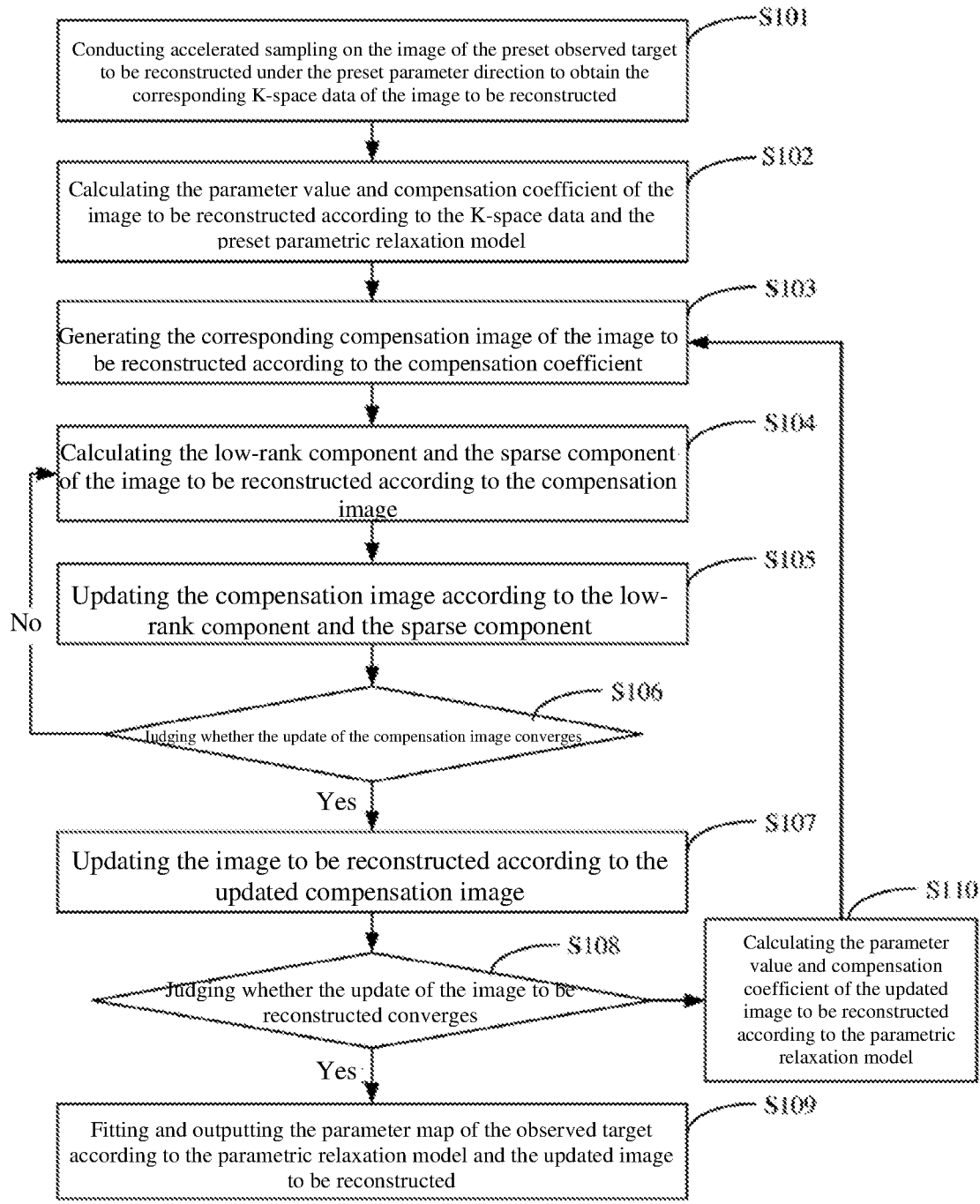
FIG. 1 is an implementation flow chart of the magnetic resonance imaging method provided in embodiment 1 of the invention.

FIG. 1 shows the implementation process of the magnetic resonance imaging method provided in embodiment 1 of the invention. For the convenience of illustration, only parts related to the embodiments of the invention are shown as follows:

In step S101, conducting accelerated sampling on the image of the preset observed target to be reconstructed under the preset parameter direction to obtain the corresponding K-space data of the image to be reconstructed.

In the embodiment of the invention, the observed object may be a patient's tissues and organs, and the parameter directions may be echo time (TE) and spin-lock time (TSL). When the parameter direction is TE, the parameter value and parameter map obtained by subsequent fitting are $T_2$ value and $T_2$ map. When the parameter direction is TSL, the parameter value and parameter map obtained by subsequent fitting are $T_{1\rho}$ value and $T_{1\rho}$ map.

In the embodiment of the invention, full sampling can be conducted in the frequency-encoding direction and variable-density undersampling can be conducted in the phase-encoding direction of the observed object to obtain the preset number of K-space data corresponding to the image to be reconstructed. K-space data are undersampled data, so the phase-parameter of the accelerated sampling for magnetic resonance imaging conforms to the random sampling theory of compressed sensing, wherein different images to be reconstructed correspond to different parameter direction values. For example, in the TSL direction, different images to be reconstructed correspond to different TSL values.

As an example, in the TSL direction, K-space data of the image to be reconstructed under different TSL values obtained by full sampling in the frequency-encoding direction and variable-density undersampling in the phase-encoding direction are undersampled data.

In step S102, calculating the parameter value and compensation coefficient of the image to be reconstructed according to the K-space data and the preset parametric relaxation model.

In the embodiment of the invention, after obtaining the K-space data under different parameter direction values by sampling, the full sampling part of the K-space data center can be converted to the image domain to obtain the corresponding image of the full sampling part of the K-space data center. The parameter value of the image to be reconstructed is obtained by fitting according to the corresponding image of the full sampling part and the parametric relaxation model. Then the compensation coefficient of the image to be reconstructed is calculated according to the parameter value. The calculated parameter value and compensation coefficient are both initial values, wherein, different parameter directions correspond to different parametric relaxation models.

As an example, when the parameter direction is TSL, the full sampling part of the K-space data center corresponding to different TSLs is be converted to the image domain. The $T_{1\rho}$ relaxation model is fitted with the image converted from the full sampling part of the K-space data center to obtain the $T_{1\rho}$ value of the image to be reconstructed. The $T_{1\rho}$ relaxation model can be indicated as:

$M_x = M_0 \exp(-TSL_k/T_{1\rho}^i)$, where, $T_{1\rho}^i$ is the $T_{1\rho}$ value of the image to be reconstructed in the $i^{th}$ update of the image to be reconstructed, $M_x$ is the image intensity of the image to be reconstructed under $TSL_k$, the $k^{th}$ spin-lock time, $M_0$ is the equilibrium image intensity obtained without applying the spin-lock pulse, k=1, 2, . . . . Specifically, the logarithm of both sides of this equation can be taken first to transform $T_{1\rho}$ relaxation model into a linear equation, i.e. a linear function of TSL, and then all pixels of the image to be reconstructed along the TSL direction can be fitted. The compensation coefficient of the image to be reconstructed is calculated according to the calculated $T_{1\rho}$ value. The formula can be $\text{Coef}^i \exp(TSL_k/T_{1\rho}^i)$, where, $\text{Coef}^i$ is the compensation coefficient of the image to be reconstructed in the $i^{th}$ update of the image to be reconstructed.

In the embodiment of the invention, as the parameter value of the image to be reconstructed is calculated according to the full sampling part of the K-space data center, its resolution is very low, so it requires iterative updates. In the subsequent iteration, the parameter values can be calculated directly according to the updated image to be reconstructed.

In step S103, generating the corresponding compensated image of the image to be reconstructed according to the compensation coefficient.

In the embodiment of the invention, the compensation coefficient can be multiplied by each pixel of the image to be reconstructed to obtain the compensated image of the image to be reconstructed. The compensated image can be indicated as $U^i=C(X^{i-1})$, and $C(\cdot)$ is the compensation operator, wherein, $X^{i-1}$ is the image sequence composed of the image to be reconstructed in the $i^{th}$ update of the image to be reconstructed.

In step S104, calculating the low-rank component and the sparse component of the image to be reconstructed according to the compensated image.

In the embodiment of the invention, after generating the corresponding compensated image of the image to be reconstructed, the low-rank component of the image to be reconstructed can be calculated according to the compensated image, the preset singular value thresholding operator and the preset initial value of the sparse component of the image to be reconstructed. Then the sparse component of the image to be reconstructed is updated according to the compensated image, the low-rank component of the image to be reconstructed and the preset soft thresholding operator, wherein the initial value of the sparse component of the image to be reconstructed can be preset as 0.

Preferably, the formula of the low-rank component $L_j$ is indicated as:

$L_j=SVT(U_{j-1}^{\ u}-S_{j-1})$ where, $SVT(\cdot)$ is the singular value thresholding operator, the calculation process of which can be indicated as $SVT_\lambda(M)=U\Lambda_\lambda(\Sigma)V^H$, $M=U\Sigma V^H$ represents singular value decomposition (SVD), U and V are matrices composed of left and right singular values respectively, $V^H$ is the conjugate transpose of V, $\Sigma$ is the diagonal matrix composed of singular values of M, $\Lambda_\lambda(\Sigma)$ represents that the maximum singular value in $\Sigma$ remains unchanged while others are 0, $L_j$ is the low-rank component of the image to be reconstructed in the $j^{th}$ update of the compensated image, $S_{j-1}$ is the sparse component of the image to be reconstructed before the $j^{th}$ update of the compensated image, and $U_{j-1}^{\ i}$ is the compensated image before the $j^{th}$ update of the compensated image in the $i^{th}$ update of the image to be reconstructed.

Preferably, the formula of the sparse component $S_j$ is indicated as:

$S_j=ST(U_{j-1}^{\ i}-L_j)$, wherein $ST(\cdot)$ is the soft thresholding operator, the calculation process of which can be indicated as $$ST(p) = \frac{p}{|p|}\max(0, |p - v|),$$

p represents an element in the image matrix, v is the preset thresholding, and $S_j$ is the sparse component after the $j^{th}$ update of the compensated image.

In step S105, updating the compensated image according to the low-rank component and the sparse component.

In the embodiment of the invention, after calculating the low-rank component and the sparse component of the image to be reconstructed, the compensated image can be updated according to the low-rank component and the sparse component to update the data fidelity term of the compensated image. Preferably, the updating formula of the compensated image is:

$U_j^i=L_j+S_j-C(E^*(EC^{-1}(L_j+S_j))-d)$, where, $U_j^i$ is the compensated image obtained after the $j^{th}$ update of the compensated image in the $i^{th}$ update of the image to be reconstructed, E is the preset encoding matrix, $E^*$ is the conjugate transpose of E, $E(X)=d$, X is the image sequence composed of the image to be reconstructed.

In step S106, judging whether the update of the compensated image converges.

In the embodiment of the invention, whether the update of the compensated image converges can be judged by judging whether the current number of updates of the compensated image reaches the preset first number thresholding, or by judging whether the difference between the compensated images before and after update is less than the preset first difference thresholding.

In the embodiment of the invention, if the update of the compensated image converges, step S107 is executed, otherwise, step S104 is executed to calculate the low-rank component and the sparse component of the said image to be reconstructed respectively.

In step S107, updating the image to be reconstructed according to the updated compensated image, In the embodiment of the invention, the image to be reconstructed can be updated by dividing each pixel in the updated compensated image by the compensation coefficient. The updating formula can be indicated as:

$X^i=C^{-1}(U_j^i)$, $X^i$ is the updated image to be reconstructed after the $i^{th}$ update of the image to be reconstructed.

In step S108, judging whether the update of the image to be reconstructed converges.

In the embodiment of the invention, whether the update of the image to be reconstructed converges can be judged by judging whether the current number of updates of the image to be reconstructed reach the preset second number thresholding, or by judging whether the difference between the images to be reconstructed before and after update is less than the preset second difference thresholding.

In the embodiment of the invention, if the update of the image to be reconstructed converges, step S109 is executed, otherwise, step S110 is executed.

In step S109, fitting and outputting the parameter map of the observed target according to the parametric relaxation model and the updated image to be reconstructed.

In the embodiment of the invention, if the update of the image to be reconstructed converges, the updated image to be reconstructed is fitted according to the parametric relaxation model to obtain corresponding parameter values of the updated image to be reconstructed. The parameter map of the observed target composed of parameter values are output, and the parameter map is the final image of the image to be reconstructed.

In step S110, calculating the parameter value and compensation coefficient of the updated image to be reconstructed according to the parametric relaxation model.

In the embodiment of the invention, if the update of the image to be reconstructed does not converge, the updated image to be reconstructed and the parametric relaxation model are fitted to obtain the parameter values of the updated image to be reconstructed. Then the compensation coefficient is calculated and updated according to the parameter value of the updated image to be reconstructed. Step S103 is executed to generate the corresponding compensated image of the image to be reconstructed according to the compensation coefficient, to continue updating the image to be reconstructed.

In the embodiment of the invention, the scanning speed and imaging speed of magnetic resonance imaging are accelerated through variable-density undersampling, parameters in the fitting process are added to the reconstruction process to guide the reconstruction of the image to be reconstructed, and the reconstruction process and the fitting process of magnetic resonance imaging are connected, which effectively improves the accuracy and efficiency of magnetic resonance imaging.

Embodiment 2

Figure 2:
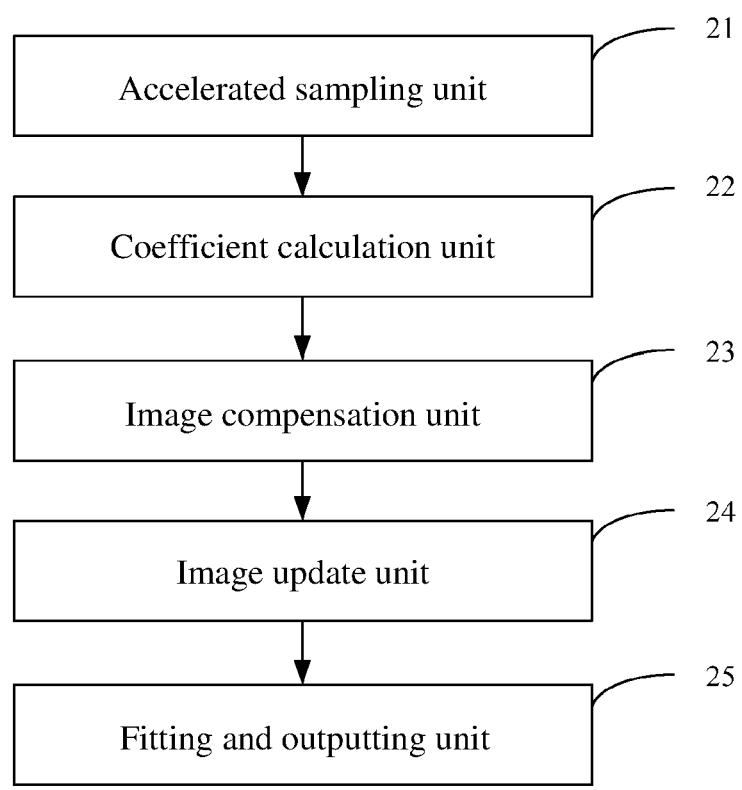
FIG. 2 is a structural diagram of the magnetic resonance imaging device provided in embodiment 2 of the invention.

FIG. 2 shows the structure of the magnetic resonance imaging device provided in embodiment 2 of the invention. For the convenience of illustration, only parts related to the embodiments of the invention are shown as follows:

Accelerated sampling unit 21 is used to conduct accelerated sampling on the image of the preset observed target to be reconstructed under the preset parameter direction to obtain the corresponding K-space data of the image to be reconstructed.

In the embodiment of the invention, the parameter directions may be echo time (TE) and spin-lock time (TSL). When the parameter direction is TE, the parameter value and parameter map obtained by subsequent fitting are $T_2$ value and $T_2$ map. When the parameter direction is TSL, the parameter value and parameter map obtained by subsequent fitting are $T_{1\rho}$ value and $T_{1\rho}$ map.

In the embodiment of the invention, full sampling can be conducted in the frequency-encoding direction and variable-density undersampling can be conducted in the phase-encoding direction of the observed object to obtain the preset number of K-space data corresponding to the image to be reconstructed. K-space data are undersampled data, so the phase-parameter of the accelerated sampling for magnetic resonance imaging conforms to the random sampling theory of compressed sensing. As an example, in the TSL direction, K-space data of the image to be reconstructed under different TSL values can be obtained by full sampling in the frequency-encoding direction and variable-density undersampling in the phase-encoding direction.

Coefficient calculation unit 22 is used to calculate the parameter value and compensation coefficient of the image to be reconstructed according to the K-space data and the preset parametric relaxation model.

In the embodiment of the invention, after obtaining the K-space data under different parameter direction values by sampling, the full sampling part of the K-space data center can be converted to the image domain to obtain the corresponding image of the full sampling part of the K-space data center. The parameter value of the image to be reconstructed is obtained by fitting according to the corresponding image of the full sampling part and the parametric relaxation model. Then the compensation coefficient of the image to be reconstructed is calculated according to the parameter value. The calculated parameter value and compensation coefficient are both initial values.

As an example, when the parameter direction is TSL, the full sampling part of the K-space data center corresponding to different TSLs is converted to the image domain. The $T_{1\rho}$ relaxation model is fitted with the image converted from the full sampling part of the K-space data center to obtain the $T_{1\rho}$ value of the image to be reconstructed. The $T_{1\rho}$ relaxation model can be indicated as:

$M_x = M_0 \exp(-TSL_k/T_{1\rho}^i)$, where, $T_{1\rho}^i$ is the $T_{1\rho}$ value of the image to be reconstructed in the $i^{th}$ update of the image to be reconstructed, $M_x$ is the image intensity of the image to be reconstructed under $TSL_k$, the $k^{th}$ spin-lock time, $M_0$ is the equilibrium image intensity obtained without applying the spin-lock pulse, k=1, 2, . . . . Specifically, the logarithm of both sides of this equation can be taken first to transform $T_{1\rho}$ relaxation model into a linear equation, i.e. a linear function of TSL, and then all pixels of the image to be reconstructed along the TSL direction can be fitted. The compensation coefficient of the image to be reconstructed is calculated according to the calculated $T_{1\rho}$. The formula can be $Coef^i = \exp(TSL_k/T_{1\rho}^i)$, where, $Coef^i$ is the compensation coefficient of the image to be reconstructed in the $i^{th}$ update of the image to be reconstructed.

In the embodiment of the invention, as the parameter value of the image to be reconstructed is calculated according to the full sampling part of the K-space data center, its resolution is very low, so it requires iterative updates. In the subsequent iteration, the parameter values can be calculated directly according to the updated image to be reconstructed.

Image compensation unit 23 is used to generate the corresponding compensated image of the image to be reconstructed according to the compensation coefficient and calculate the low-rank component and the sparse component of the image to be reconstructed according to the compensated image.

In the embodiment of the invention, the compensation coefficient can be multiplied by each pixel of the image to be reconstructed to obtain the compensated image of the image to be reconstructed. The compensated image can be indicated as $U^i = C(X^{i-1})$, and $C(\cdot)$ is the compensation operator, wherein $X^{i-1}$ is the image sequence composed of the image to be reconstructed in the $i^{th}$ update of the image to be reconstructed. Then, the low-rank component of the image to be reconstructed can be calculated according to the compensated image, the preset singular value thresholding operator and the preset initial value of the sparse component of the image to be reconstructed. Then the sparse component of the image to be reconstructed is updated according to the compensated image, the low-rank component of the image to be reconstructed and the preset soft thresholding operator.

Preferably, the formula of the low-rank component $L_j$ is indicated as:

$L_j = SVT(U_{j-1}^i - S_{j-1})$, wherein $SVT(\cdot)$ is the singular value thresholding operator, the calculation process of which can be indicated as $SVT_\lambda(M) = U\Lambda_\lambda(\Sigma)V^H$, $M = U\Sigma V^H$ represents singular value decomposition (SVD), U and V are matrices composed of left and right singular values respectively, $V^H$ is the conjugate transpose of V, $\Sigma$ is the diagonal matrix composed of singular values of M, $\Lambda_\lambda(\Sigma)$ represents that the maximum singular value in $\Sigma$ remains unchanged while others are 0, $L_j$ is the low-rank component of the image to be reconstructed in the $j^{th}$ update of the compensated image, $S_{j-1}$ is the sparse component of the image to be reconstructed before the $j^{th}$ update of the compensated image, and $U_{j-1}^i$ is the compensated image before the $j^{th}$ update of the compensated image in the $i^{th}$ update of the image to be reconstructed.

Preferably, the formula of the sparse component $S_j$ is indicated as:

$S_j = ST(U_{j-1}^i - L_j)$, where, $ST(\cdot)$ is the soft thresholding operator, the calculation process of which can be indicated as $$ST(p) = \frac{p}{|p|}\max(0, |p-v|),$$

p represents an element in the image matrix, v is the preset thresholding, and $S_j$ is the sparse component after the $j^{th}$ update of the compensated image.

Image update unit 24 is used to update the compensated image according to the low-rank component and the sparse component, and judge whether the update of the compensated image converges. If the update converges, the image to be reconstructed is updated according to the updated compensated image; otherwise, image compensation unit 23 is triggered to execute the step of calculating the low-rank component and the sparse component of the image to be reconstructed respectively.

In the embodiment of the invention, after calculating the low-rank component and the sparse component of the image to be reconstructed, the compensated image can be updated according to the low-rank component and the sparse component to update the data fidelity term of the compensated image. Preferably, the updating formula of the compensated image is:

$U_j^i = L_j + S_j - C(E^*(EC^{-1}(L_j + S_j)) - d)$, where, $U_j^i$ is the compensated image obtained after the $j^{th}$ update of the compensated image in the $i^{th}$ update of the image to be reconstructed, E is the preset encoding matrix, E* is the conjugate transpose of E, E(X)=d, X is the image sequence composed of the image to be reconstructed.

In the embodiment of the invention, whether the update of the compensated image converges can be judged by judging whether the current number of updates of the compensated image reaches the preset first number thresholding, or by judging whether the difference between the compensated images before and after update is less than the preset first difference thresholding.

In the embodiment of the invention, if the update of the compensated image converges, the image to be reconstructed can be updated by dividing each pixel in the updated compensated image by the compensation coefficient. The updating formula can be indicated as:

$X^i = C^{-1}(U_j^i)$, $X^i$ is the updated image to be reconstructed in the $i^{th}$ update of the image to be reconstructed. If the update of the compensated image does not converge, image compensation unit 23 is triggered to execute the step of calculating the low-rank component and the sparse component of the image to be reconstructed respectively.

Fitting and outputting unit 25 is used to judge whether the update of the image to be reconstructed converges. If the update converges, the parameter map of the observed target is fitted and output according to the parametric relaxation model and the updated image to be reconstructed, otherwise, the parameter value and compensation coefficient of the updated image to be reconstructed is calculated according to the parametric relaxation model, and image compensation unit 23 is triggered to execute the step of generating the corresponding compensated image of the image to be reconstructed according to the compensation coefficient.

In the embodiment of the invention, whether the update of the image to be reconstructed converges can be judged by judging whether the current number of updates of the image to be reconstructed reach the preset second number thresholding, or by judging whether the difference between the images to be reconstructed before and after update is less than the preset second difference thresholding.

In the embodiment of the invention, if the update of the image to be reconstructed converges, the updated image to be reconstructed is fitted according to the parametric relaxation model to obtain corresponding parameter values of the updated image to be reconstructed. The parameter map of the observed target composed of parameter values are output, and the parameter map is the final image of the image to be reconstructed. If the update of the image to be reconstructed does not converge, the updated image to be reconstructed and the parametric relaxation model are fitted to obtain the parameter values of the updated image to be reconstructed. Then the compensation coefficient is calculated and updated according to the parameter value of the updated image to be reconstructed. Image compensation unit 23 is triggered to execute the step of generating the corresponding compensated image of the image to be reconstructed according to the compensation coefficient.

Figure 3:
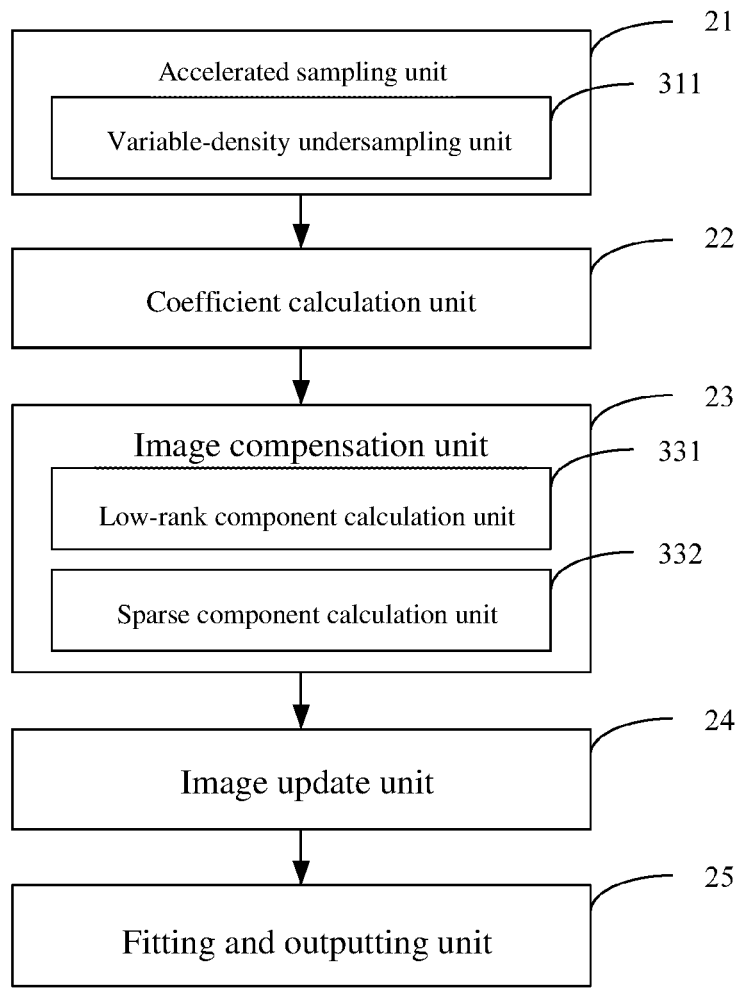
FIG. 3 is an optimal structural diagram the magnetic resonance imaging device provided in embodiment 2 of the invention.

Preferably, as shown in FIG. 3, accelerated sampling unit 21 comprises:

Variable-density undersampling unit 311 is used to conduct full sampling in the frequency-encoding direction and variable-density undersampling in the phase-encoding direction of the observed object to obtain the preset number of K-space data of the image to be reconstructed.

Preferably, image compensation unit 23 comprises:

Low-rank component calculation unit 331 is used to calculate the low-rank component of the image to be reconstructed according to the compensated image, the preset singular value thresholding operator and the preset initial value of the sparse component of the image to be reconstructed; and Sparse component calculation unit 332 is used to update the sparse component of the image to be reconstructed according to the compensated image, the low-rank component of the image to be reconstructed and the preset soft thresholding operator.

In the embodiment of the invention, the scanning speed and imaging speed of magnetic resonance imaging are accelerated through variable-density undersampling, parameters in the fitting process are added to the reconstruction process to guide the reconstruction of the image to be reconstructed, and the reconstruction process and the fitting process of magnetic resonance imaging are connected, which effectively improves the accuracy and efficiency of magnetic resonance imaging.

In the embodiment of the invention, each unit of the magnetic resonance imaging device can be realized by corresponding hardware or software unit. Each unit may be an independent software or hardware unit, or a integrated software and hardware unit, which shall not be used to limit the invention.

Embodiment 3

Figure 4:
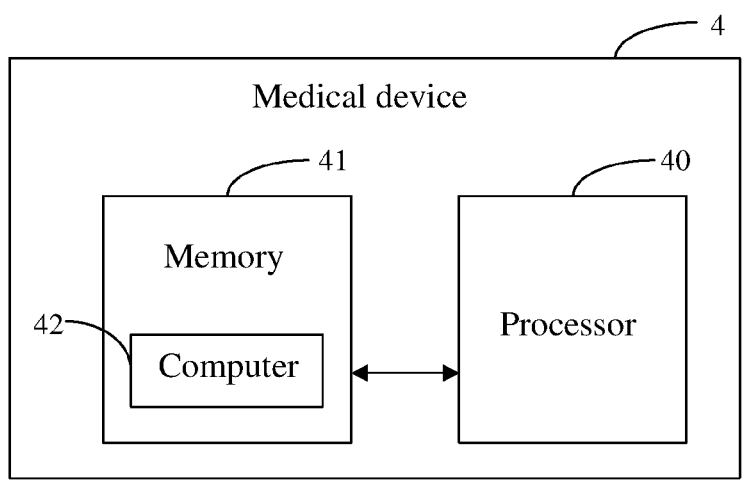
FIG. 4 is the structure diagram of the medical device provided in embodiment 3 of the invention.

FIG. 4 shows the structure of the medical device provided in embodiment 3 of the invention. For the convenience of illustration, only parts related to the embodiments of the invention are shown.

The medical device 4 in the embodiment of the invention comprises a processor 40, a memory 41, and a computer program 42 stored in the memory 41 and capable of running on the processor 40. The processor 40 executes the computer program 42 to implement the steps in the aforesaid embodiment of the method, such as steps S101 to S110 shown in FIG. 1. Or, the processor 40 executes the computer program 42 to implement the functions of the units in the aforesaid embodiment of the device, such as functions of units 21 to 25 shown in FIG. 2.

In the embodiment of the invention, the scanning speed and imaging speed of magnetic resonance imaging are accelerated through variable-density undersampling, parameters in the fitting process are added to the reconstruction process to guide the reconstruction of the image to be reconstructed, and the reconstruction process and the fitting process of magnetic resonance imaging are connected, which effectively improves the accuracy and efficiency of magnetic resonance imaging.

Embodiment 5

The embodiment of the invention provides a computer readable storage medium which stores a computer program, which stores a computer program, which is executed by the processor to implement steps in the aforesaid embodiment of the method, such as, steps S101 to S110 shown in FIG. 1. Or the computer program is executed by the processor to implement the functions of the units in the aforesaid embodiment of the device, such as functions of units 21 to 25 shown in FIG. 2.

In the embodiment of the invention, the scanning speed and imaging speed of magnetic resonance imaging are accelerated through variable-density undersampling, parameters in the fitting process are added to the reconstruction process to guide the reconstruction of the image to be reconstructed, and the reconstruction process and the fitting process of magnetic resonance imaging are connected, which effectively improves the accuracy and efficiency of magnetic resonance imaging.

The computer readable storage medium in the embodiment of the invention may include any entity or device capable of carrying computer program code, or recording medium, such as ROM/RAM, disk, optical disk and flash memory, etc.

The above description is only an embodiment of the present invention; it is not intended to limit the scope of the invention. Any modification, equivalent substitution and improvement with the spirit and principle of this invention shall be included in the scope of protection of the invention.

The invention claimed is:

1. A magnetic resonance imaging method, wherein the steps comprise:
conducting accelerated sampling on the image of the preset observed target to be reconstructed under the preset parameter direction to obtain the corresponding K-space data of the said image to be reconstructed;
calculating the parameter value and compensation coefficient of the said image to be reconstructed according to the said K-space data and the preset parametric relaxation model;
generating the corresponding compensated image of the said image to be reconstructed according to the said compensation coefficient and calculate the low-rank component and the sparse component of the said image to be reconstructed according to the said compensated image;
updating the compensated image according to the said low-rank component and the said sparse component, and judge whether the update of the said compensated image converges; if the update converges, updating the said image to be reconstructed according to the said updated compensated image; otherwise, skipping to the step of calculating the low-rank component and the sparse component of the said image to be reconstructed respectively;
judging whether the update of the said image to be reconstructed converges; if the update converges, fitting and outputting the parameter map of the said observed target according to the said parametric relaxation model and the updated image to be reconstructed, otherwise, calculating the parameter value and compensation coefficient of the updated image to be reconstructed according to the said parametric relaxation model, and skipping to the step of generating the corresponding compensated image of the said image to be reconstructed according to the said compensation coefficient.

2. The said method as in claim 1, wherein the steps of conducting accelerated sampling on the image of the preset observed target to be reconstructed under the preset parameter direction comprise:
conducting full sampling in the frequency-encoding direction and variable-density undersampling in the phase-encoding direction of the said observed object to obtain the preset number of K-space data of the said image to be reconstructed.

3. The said method as in claim 1, wherein the steps of calculating the parameter value and compensation coefficient of the said image to be reconstructed according to the said K-space data and the preset parametric relaxation model comprise:
converting the full sampling part of the said K-space data center to the image domain to obtain the corresponding image of the full sampling part of the said K-space data center;
Fitting to obtain the parameter value of the said image to be reconstructed according to the said corresponding image of the full sampling part and the said parametric relaxation model, and calculating the said compensation coefficient according to the parameter value of the said image to be reconstructed.

4. The said method as in claim 1, wherein the steps of calculating the low-rank component and the sparse component of the said image to be reconstructed according to the said compensated image comprise:
calculating the low-rank component of the said image to be reconstructed according to the said compensated image, the preset singular value thresholding operator and the preset initial value of the sparse component of the said image to be reconstructed;
updating the sparse component of the said image to be reconstructed according to the said compensated image, the low-rank component of the said image to be reconstructed and the preset soft thresholding operator.

5. The said method as in claim 1, wherein the steps of updating the said compensated image according to the said low-rank component and sparse component comprise:
Updating the data fidelity term of the said compensated image according to the said low-rank component and the sparse component; the updating formula is:
$U_j^i = L_j + S_j - C(E^*(EC^{-1}(L_j+S_j))-d)$, where, $U_j^i$ is the said compensated image obtained after the $j^{th}$ update of the said compensated image in the $i^{th}$ update of the said image to be reconstructed, $L_j$ is the said low-rank component in the $j^{th}$ update of the said compensated image, $S_j$ is the said sparse component of the $j^{th}$ update of the said compensated image, E is the preset encoding matrix, E* is the conjugate transpose of E, E(X)=d, X is the image sequence composed of the said image to be reconstructed.

6. A medical device, which comprises a memory, a processor, and a computer program stored in the memory and capable of running on the said processor, wherein the steps comprise any of the said methods as in claim 1 when the said processor executes the said computer program.

7. A non-transitory computer readable storage medium, which stores a computer program, wherein the steps comprise any of the said methods as in claim 1 when the said computer program is executed by the processor.

8. A magnetic resonance imaging device, wherein the device comprises:
   Accelerated sampling unit is used to conduct accelerated sampling on the image of the preset observed target to be reconstructed under the preset parameter direction to obtain the corresponding K-space data of the said image to be reconstructed;
   Coefficient calculation unit is used to calculate the parameter value and compensation coefficient of the said image to be reconstructed according to the said K-space data and the preset parametric relaxation model;
   Image compensation unit is used to generate the corresponding compensated image of the said image to be reconstructed according to the said compensation coefficient and calculate the low-rank component and the sparse component of the said image to be reconstructed according to the compensated image;
   Image update unit is used to update the compensated image according to the said low-rank component and the said sparse component, and judge whether the update of the said compensated image converges; if the update converges, the said image to be reconstructed is updated according to the said updated compensated image; otherwise, the image compensation unit is triggered to execute the step of calculating the low-rank component and the sparse component of the said image to be reconstructed respectively; and
   Fitting and outputting unit is used to judge whether the update of the said image to be reconstructed converges; if the update converges, the parameter map of the said observed target is fitted and output according to the said parametric relaxation model and the said updated image to be reconstructed, otherwise, the parameter value and compensation coefficient of the updated image to be reconstructed is calculated according to the said parametric relaxation model, and the said image compensation unit is triggered to execute the step of generating the corresponding compensated image of the said image to be reconstructed according to the said compensation coefficient.

9. The said device as in claim 8, wherein the accelerated sampling unit comprises:
   Variable-density undersampling unit is used to conduct full sampling in the frequency-encoding direction and variable-density undersampling in the phase-encoding direction of the said observed object to obtain the preset number of K-space data of the said image to be reconstructed.

10. The said device as in claim 8, wherein the image compensation unit comprises:
    Low-rank component calculation unit is used to calculate the low-rank component of the said image to be reconstructed according to the said compensated image, the preset singular value thresholding operator and the preset initial value of the sparse component of the said image to be reconstructed; and
    Sparse component calculation unit is used to update the sparse component of the said image to be reconstructed according to the said compensated image, the low-rank component of the said image to be reconstructed and the preset soft thresholding operator.

* * * * *